United States Patent [19]

Roeder et al.

[11] 4,383,446

[45] May 17, 1983

[54] METHOD FOR NON-DESTRUCTIVELY TESTING CONSTRUCTION ELEMENTS

[75] Inventors: Eckhard Roeder, Lesumer Heerstr. 5, 2820 Bremen 77, Fed. Rep. of Germany; Wolfgang Flake, Bremen, Fed. Rep. of Germany

[73] Assignee: Eckhard Roeder, Bremen, Fed. Rep. of Germany

[21] Appl. No.: 248,601

[22] Filed: Mar. 27, 1981

[30] Foreign Application Priority Data

Apr. 2, 1980 [DE] Fed. Rep. of Germany ....... 3012774

[51] Int. Cl.³ ........................................... G01N 29/04
[52] U.S. Cl. ................................... 73/579; 73/1 DV; 73/620
[58] Field of Search ................. 73/579, 620, 624, 629, 73/1 DV

[56] References Cited

U.S. PATENT DOCUMENTS 2,716,887 9/1955 Smith ..................................... 73/579
3,872,443 3/1975 Ott ......................................... 73/579

Primary Examiner—Stephen A. Kreitman
Attorney, Agent, or Firm—Sughrue, Mion, Zinn, Macpeak & Seas

[57] ABSTRACT

A method of non-destructively testing construction elements accessible from only one side by measuring their resonant oscillations to detect flaws in them without scanning. A test piece (1) is excited with a narrow band ultrasonic oscillation whose frequency is varied; the amplitudes of the resonant oscillations are measured and plotted in an xy coordinate system against the frequency of the exciting ultrasonic oscillations.

2 Claims, 1 Drawing Figure

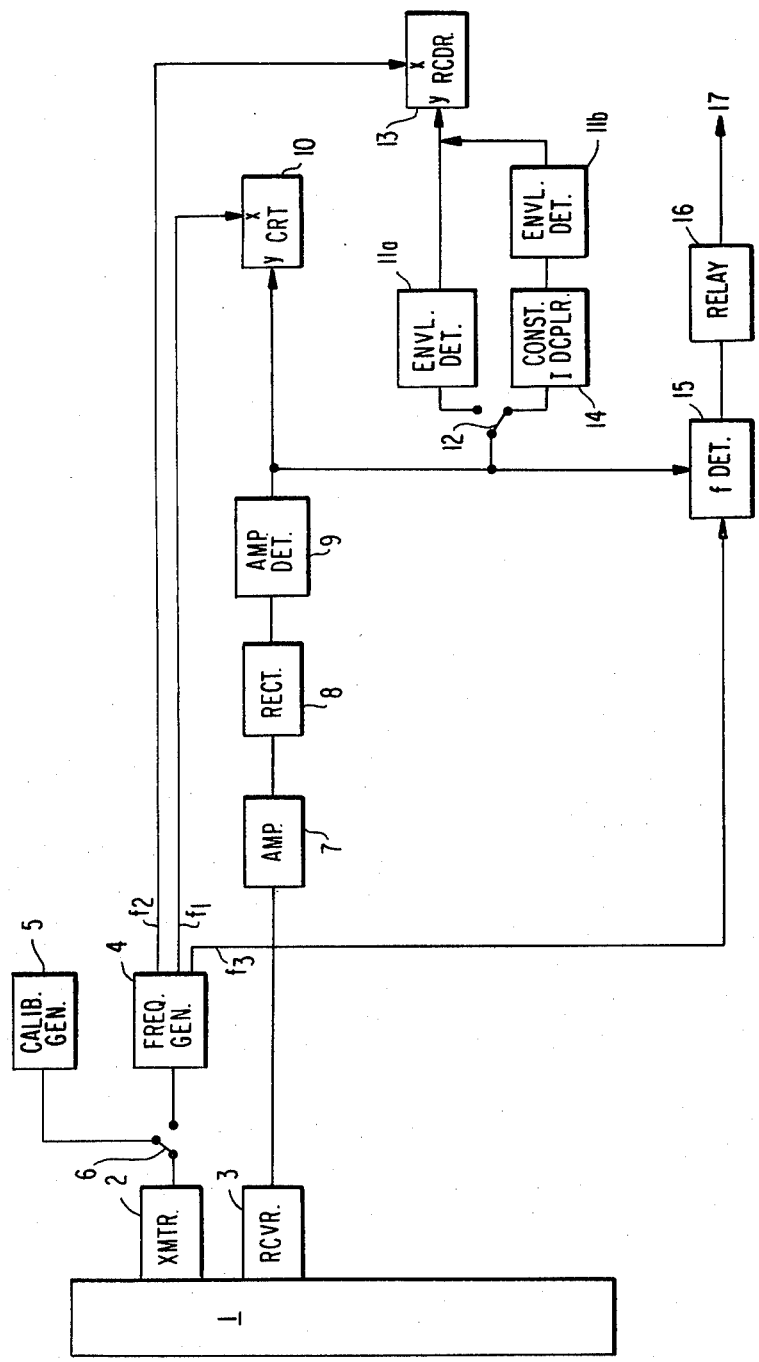

METHOD FOR NON-DESTRUCTIVELY TESTING CONSTRUCTION ELEMENTS

BACKGROUND OF THE INVENTION

The invention relates to a method for non-destructively testing construction elements by measuring their resonant vibrations.

The invention is intended primarily for quality control and damage analysis to test and monitor construction materials and components. Unwanted joint changes and cracks can occur in the manufacture and handling or stressing of construction components. To prevent them from subsequently failing it is necessary to examine and detect these changes without destroying the component.

It is known that joint changes in construction components affect the modulus of elasticity, the density, the transverse contraction and influence the distribution of sonic transmissions. When a component is caused to vibrate characteristic resonances occur as a result of its geometry, which provides information about the condition of the component. This also applies to the formation of cracks because this causes a change in the spring-/mass-system. These flaws produce changes in the formation of vibration characteristics of the component.

The known test methods which operate with ultrasonic radiation rely on sending a sonic impulse into the component and measuring changes in its reflected echo caused by flaws in the component. In these methods the transmitted impulse has a constant frequency and must decay as quickly as possible so that the echo, which is reflected by the back wall of the component or the flaws in front of it, can be received. To this end it is necessary that the transmitted impulse strike the flaw as directly as possible. To detect internal flaws a component must be scanned along its surface. Flaws can only be recognized if they can be directly reached by the transmitted signal. Therefore, it is desirable for rapid flaw detection in components to use a method which makes integral measurement of hidden flaws in the component possible.

SUMMARY OF THE INVENTION

The object of the invention is to detect flaws without having to scan the component in order to be able to examine components which are only accessible from one side. This object is solved according to the invention in that the test piece is excited with a narrow band ultrasonic oscillation whose frequency is varied; the amplitudes of the resonant oscillations are measured and plotted in an xy coordinate system against the frequency of the exciting ultrasonic oscillation.

The frequency of the exciting oscillation can be varied in stages for a fully automtic evaluation, or continuously for a visual depiction. To increase the resolution of the resonant amplitudes with each respective frequency, in addition to the absolute height of the amplitudes, their changes can also be directly detected which renders even very small flaws in the sample detectable. It is therefore advantageous according to another aspect of the invention to decouple the constant voltage of the measured amplitudes of the resonant oscillations and subsequently form an envelope, whereby the deviations in amplitude are directly measured.

According to a further aspect of the invention it is advantageous if the frequency of the exciting ultrasonic oscillation is varied in stages, and limiting values for the amplitudes of the resonant oscillations of the component are set for each stage to allow fully automatic evaluation independent of subjective influences of the examining personnel.

The decisive advantages of the method according to the invention are that the sample is not scanned, and in addition hidden flaws are discovered. A further advantage is that the test can be integrated fully automatically into a production process by the use of decision thresholds.

BRIEF DESCRIPTION OF THE DRAWINGS

To facilitate a better understanding of the invention reference is made to the single drawing FIGURE, which shows an exemplary block diagram of an electronic circuit for practicing the invention.

DETAILED DESCRIPTION OF THE PREFERRED EMBODIMENT

Referring now to the drawing, a construction element test piece 1 is excited by a transmitter 2 with a narrow band ultrasonic oscillation from a frequency generator 4, and a receiver 3 detects resonant oscillations of the test piece.

A calibration signal generator 5 can be switched into transmitter 2 by a transfer switch 6 in place of the frequency generator 4, which monitors the decoupling of the transmitter 2 and the receiver 3 to the test piece 1.

The frequency generator 4 supplies a frequency $f_1$ to the x-coordinate drive of a CRT screen 10, and/or a frequency $f_2$ to the x-coordinate drive of a printer 13. The frequencies $f_1$ and $f_2$ are continuously varied.

The frequency generator 4 may, in addition, supply a frequency $f_3$ in stages to an adjustable threshold detector 15.

The resonant oscillations detected by the receiver 3 from the test piece 1 are fed through an amplifier 7, a rectifier 8, and an amplitude detector 9. The amplitudes of the resonant oscillations measured by the amplitude detector are sent to the y-coordinate drive of the CRT screen 10 to thus implement a functional display of any flaws in the test piece.

The resonant oscillation amplitudes measured in the detector 9 may also be supplied through a transfer switch 12 to either an envelope detector 11a with a time constant of "one" or to an envelope detector 11b with a time constant of "two" through a constant current decoupler 14. The outputs of both envelope detectors are fed to the y-coordinate drive of the printer 13 to document the measured flaw patterns.

Finally, to be fully automatically evaluated the output of the amplitude detector 9 is also fed to the threshold detector 15 so that it can be automatically compared with a preset limit value. If the limit value is exceeded a control relay 16 is actuated which in turn generates an alarm signal 17.

What is claimed is:

1. Method for non-destructively testing construction elements by measuring their resonant oscillations, comprising: exciting a test piece (1) with a narrow band ultrasonic oscillation, varying the oscillation frequency, measuring the amplitudes of resonant oscillations in the test piece, and plotting said resonant amplitudes in an xy coordinate system against the frequency of the exciting ultrasonic oscillations, wherein resonant amplitude deviations are directly measured by a constant voltage decoupling of the measured amplitudes of the resonant oscillations, and amplitude envelopes are formed.

2. Method according to claim 1, wherein the frequency of the exciting ultrasonic oscillation is varied in stages, and limit values for the amplitudes of the resonant oscillations of the construction element are set for each stage for purposes of fully automatic evaluation.

* * * * *